United States Patent [19]

Teodorescu et al.

[11] Patent Number: 4,797,363

[45] Date of Patent: Jan. 10, 1989

[54] BACTERIOPHAGES AS RECOGNITION AND IDENTIFICATION AGENTS

[75] Inventors: Marius C. Teodorescu, Westchester; Alexandre M. Gaspar, Chicago, both of Ill.

[73] Assignee: Board of Trustees, University of Illinois, Urbana, Ill.

[21] Appl. No.: 885,328

[22] Filed: Jul. 14, 1986

Related U.S. Application Data

[63] Continuation of Ser. No. 591,136, Mar. 19, 1984, abandoned.

[51] Int. Cl.[4] .......................... C12N 7/00; C12N 7/02; C12N 13/00; C12Q 1/70

[52] U.S. Cl. .......................................... 435/235; 435/5; 435/239; 435/173; 436/501; 436/802

[58] Field of Search ....................... 435/5, 6, 7, 29, 34, 435/39, 810, 172.1, 173, 239, 235; 436/519, 527, 501, 802

[56] References Cited

U.S. PATENT DOCUMENTS

| | | | |
|---|---|---|---|
| 3,094,466 | 6/1963 | Schwartz | 435/5 |
| 3,553,310 | 1/1971 | Csizmas et al. | 436/519 X |
| 3,562,384 | 2/1971 | Arquilla | 436/519 X |
| 3,717,705 | 2/1973 | Haimovich et al. | 436/519 |
| 4,104,126 | 8/1978 | Young | 435/5 |
| 4,105,598 | 8/1978 | Yen et al. | 435/34 X |
| 4,189,466 | 2/1980 | Ainis et al. | 436/519 X |
| 4,223,005 | 9/1980 | Teodorescu et al. | 436/519 |
| 4,282,315 | 8/1981 | Luderer et al. | 435/5 |
| 4,298,689 | 11/1981 | Doyle et al. | 435/34 |
| 4,347,311 | 8/1982 | Schmitz | 435/5 |
| 4,434,150 | 2/1984 | Azad et al. | 424/83 X |
| 4,474,877 | 10/1984 | Imagawa et al. | 435/810 X |
| 4,508,829 | 4/1985 | Sulitzeanu | 436/519 X |
| 4,511,662 | 4/1985 | Baran et al. | 436/519 X |
| 4,552,812 | 11/1985 | Margel et al. | 436/501 X |

OTHER PUBLICATIONS

Urbain et al, Progress in Immunology IV, New York, Academic Press, 1980, pp. 81–93.

Ghetie et al, "Multivalent Hybrid Antibody", Molecular Immunology, vol. 17, 1980, pp. 395–401.

*Primary Examiner*—Robert J. Warden
*Assistant Examiner*—Randall E. Deck
*Attorney, Agent, or Firm*—Philip Hill

[57] ABSTRACT

Bacteriophages are employed as agents for recognition and identification of molecules and cellular materials, using their ability to recognize their bacterial host, by coating them with antibodies or by selecting them to perform in a manner analogous to antibodies. Visibility for identification is effected by incorporating a fluorescent agent, a radioisotope, a metal, an enzyme, or other staining material. The bacteriophage are prepared so as to bind to the molecular or cellular material through either the tail or head segment of the bacteriophage.

6 Claims, No Drawings

BACTERIOPHAGES AS RECOGNITION AND IDENTIFICATION AGENTS

The invention described herein was sponsored in part by the National Cancer Institute, under Grant CA 21399, which has certain rights thereto.

This application is a continuation of application Ser. No. 591,136, filed Mar. 19, 1984, now abandoned.

BACKGROUND OF THE INVENTION

At the present time antibodies are used almost exclusively to identify molecular and cellular structures that do not reveal themselves otherwise. For example, they are used to distinguish one protein from another, one polysaccharide from another, or one cell from another. The interaction between the antibodies and the "identified" structure may be measured by a variety of methods aimed at making visible the presence of the antibodies.

In some tests, an antibody bound to the structure, cell, or solid phase to be identified is directly made visible. More often, a second antibody is made visible and is directed against the first antibody. In addition, protein A of *Staphylococcus aureus,* Cowan I strain, is made visible and it binds to the first antibody. Another class of reagents used to make the antibody visible is represented by biotin and avidin which recognize each other and can be used in conjunction with antibodies. Fluorescent material, enzymes, radioactive materials, large particles, such as erythrocytes, or beads have been used to make the antibody visible directly or indirectly.

Each of these procedures has shortcomings and limitations which may be illustrated by the use of fluorescent materials to visualize the antibody. If the amount of antibody bound by a cell is too small the fluorescent reagents fail to detect it. This creates analytical difficulties, particularly when using double laser flow cytometry or fluorometric systems. Further, the fluorescence obtained with any antibody system on tissue sections is not very bright. This difficulty may be overcome by using enzymes coupled to the antibody. However, multiple steps in the staining process are always required.

Solutions to the problem have included the use of fluorescent bacteria or fluorescent beads. The former have a limited use in fluorescence analysis due to difficulties in removing unbound excess bacteria and also due to a significant change in the light scattering profile of the cell surface, making impossible the proper use of flow cytometry. The latter tend to stick to cells, are difficult to produce or too expensive, and they are also big enough to cause changes in the light scattering profile of the cell surface. Moreover, in fluorometric systems that require filtration and washing, the excess particles or bacteria are difficult, if not impossible, to remove. The use of reagents such as bacteria or coloidal gold for stained, fixed preparations of cells is limited to microscopy. Accordingly, there has been a need for another class of reagents that will combine the advantages of antibodies with those of particles that can be used for flow cytometry for tissue sections or for solid phase assays for soluble materials. Such solid phases may be those used in kits for measuring antigens or antibodies in solutions, either directly or in competitive assays. It has not been possible to have a reagent that combined all the advantages of antibodies, such as penetrability and specificity, with those of particles, such as visibility. In fact, there was a need for a reagent that works like an antibody but is much larger in size, although not so large as to obscure the structures to be identified. Such a reagent must remain out of some structures, such as fixed cells or tissues, and excess reagent must be readily removed.

It is likely that bacteriophages have been considered either too small to serve as efficient carriers or to be sticky in a nonspecific way, particularly due to their tail fibers. The only use that bacteriophages have had in identification experiments has been to use them as viruses for their bacterial host or to put antigens on their surface, usually through a mild chemical process of coupling, and then to use antibodies against these antigens to block the ability of the bacteriophage to infect bacteria in bacteriophage neutralization systems. Thus, bacteriophage was used only as living virus in Haimovich, et al., U.S. Pat. No. 3,717,705 and in Young, U.S. Pat. No. 4,104,126. It was not employed as a carrier for antibodies as an identification and staining reagent. It is likely that one skilled in the art has been deterred from using the phage for any other assays with antibodies, for the reasons given above.

Luderer, et al., U.S. Pat. No. 4,282,315, proposed the use of radiolabelled animal viruses to detect receptors on materials that are natural receptors of these viruses or mimic such receptors. Essentially the animal viruses were selected for their natural affinity for certain receptor materials and were then removed and multiplied. This was essentially designed either to identify virus receptors or for hemagglutination purposes, i.e., there was a clear similarity between the receptors for virus and those identified. Bacteriophages, which are bacterial viruses, have not been considered in this category for these obvious reasons. First, they are not used for any hemagglutination or hemagglutination inhibition assays; these are based on characteristics of only certain animal viruses. Second, it is well known that bacteriophages have specialized structures, most with the appearance of a tail, that are used for recognition of the receptor on bacteria, leading to infection. It is well known that once this tail binds to its receptor, even when it is not on bacteria but in solution, the nucleic acid is evacuated and the virus becomes non-infectious. Thus, such a method of selection would have been considered impossible according to the techniques of the Luderer, et al., patent. On the other hand, the bacteriophage would not have been considered for selection for its binding with the head protein since mutations in head proteins are considered lethal for the bacteriophage. This may explain why the Luderer, et al., patent did not consider the bacteriophage as a possible alternative, despite the fact that bacteriophages are much cheaper to produce and are easily generated in very large quantity, e.g., orders of magnitude larger than animal viruses.

SUMMARY OF THE INVENTION

This invention relates to a novel method for the identification and quantification of molecular and cellular materials of both procaryatic and eucaryatic cells wherein a test sample is combined with a selected bacteriophage under binding conditions to provide in the test sample a conjugate phase, comprising bacteriophage coupled with the molecule or cells sought to be identified. A visibility agent is incorporated in the bacteriophage, either before or after the binding step, to improve greatly the recognition of the test material in conventional analytical assay techniques. In the practice of this invention the bacteriophage may be selected to bind through its head or through its tail. In the latter instance, this is accomplished by "external imaging" whereby the bacteriophage is modified to perform in the manner of an antibody.

Generally, mutants of the bacteriophage are employed. The method of this invention can be adapted to the analysis of proteins, carbohydrates, lectins, bacteria of various types, pathogens, and miscellaneous molecular or cellular materials present in tissues, cells or fluids.

It is a further object of this invention to provide assay kits, comprising selected bacteriophage and suitable test means for providing the test material in a form suitable for use in any selected analytical instrument.

DESCRIPTION OF THE INVENTION

The recognition of a structure by an agent of identification such as an antibody can be subdivided into two parts, the "intelligence", i.e., the specific site that binds a complementary structure and the "visualizer", i.e., the structure that is somehow made visible. For example, in the case of antibody-coated fluorescent beads or bacteria, the "intelligence" is given by the antibody and the "visualizer" by bacteria or by the beads. When only antibodies are use, the "intelligence" is provided by the combining site of the antibody molecule and the "visualizer" by the rest of the molecule with its molecular attachments (fluorescent, radioactive, etc.). To provide additional "visualizer" according to this invention, the antibodies are coupled to bacteriophages. This coupling may be covalent, as with glutaraldehyde or bifunctional reagents, or noncovalent, as with hybrid antibodies. Also, according to this invention, the bacteriophages can be selected and constructed to provide the "intelligence", i.e., to function as antibodies, and also to carry the "visualizer".

In the identification of bacteria in pathologic fluids it takes time to grow and identify the bacteria and, in many cases, bacteria cannot be grown in culture. For these cases, bacteriophages are made visible and are either coated with antibodies or binded naturally through their receptor.

In the practice of the method f this invention, bacteriophages are used as the visualizer, or carrier of intelligence, which is provided by the antibody. Antibodies may be coupled to bacteriophages chemically, employing bifunctional reagents, such as glutareldehyde or other covalent or non-covalent coupling agents. Bacteriophages are coated with avidin or biotin to bind to the antibody that has biotin or avidin, respectively. The binding is achieved through biotin-avidin recognition.

Bacteriophages serve as visualizers by linking to the structure to be identified with the help of hybrid antibodies. These are directed with one combining site against the bacteriophage and with the other against a first antibody or the structure to be identified. The bacteriophage can also be coupled to lectins or carbohydrates for recognition of the respective complementary structures.

The visualizer provided by the bacteriophage is obtained with the help of fluorescent dyes, other dyes, radioactive isotopic material, enzymes, or metals such as silver or gold. The bacteriophage may also be engineered to contain the enzyme of use.

Bacteriophages can be selected to provide both intelligence and visualizer through genetic manipulation, providing them with a "combining site". After mutation, the bacteriophages are then selected for the property of the head to bind to molecules such as immunoglobulins or to glycoproteins or proteins of animal cells. The mutants are obtained, for example, by ultraviolet light irradiation of both bacteriophage and bacteria, followed by the growth of the bacteriophage. The bacteriophage is harvested, purified and the selection pressure is applied; namely, binding to cell surfaces or to molecules coupled to a solid phase. The bacteriophage is made fluorescent for cell surface identification directly or after the cell has been treated with the antibody recognized by the bacteriophage. The lethal nature of head mutations is avoided by using very large numbers of particles and by selecting temperature-resistant mutants, thus selecting for very rare events that are still compatible with bacteriophage survival.

Another set of mutants can be prepared by using the tail's ability to bind to a specific structure on the surface of bacteria. By mutation and selection bacteriophages are selected which have their tail capable of recognizing particular structures. This is done by "external imaging", an unobvious analogy with internal imaging in the antiidiotype network of antibodies, as discussed by Urbain, et al., *Progress in Immunology,* 1980, Academic Press, Vol. IV, pp. 81–92. The molecule to be identified, "X", is injected in an animal and antibodies are made against it. The purified anti "X" antibodies are coupled to a solid phase and treated with a very large number of bacteria. These bacteria are selected for resistance to bacteriophage "Y" from bacteriophage-sensitive parental strain. These bacteriophage-resistant bacteria lack receptors for the bacteriophage. Bacteria that bind to these antibodies are selected and grown so that they will have a structure that mimics "X". The selection of bacteria capable of expressing "X"-like structures can be verified by their ability to bind to purified anti "X" on the bacteria It is most unexpected that such a structure can be the receptor for the bacteriophage. These bacteria are then mixed, in approximately equal parts, with the bacteriophage-sensitive bacteria which had been UV-irradiated and treated with mutagenized (e.g., UV-irradiated) bacteriophage. The mutant bacteriophages emerging from sensitive bacteria, which are capable of recognizing the receptor on the bacteriophage-resistant bacteria, will grow in these bacteria. Thus, all confluent lysis will be turbid since only the bacteriophage-sensitive bacteria are lysed, except for a few clear plaques in which both bacteria will be lysed as a result of the mutant. The plaques are removed to an absorbent material and the mutants that recognize "X" are detected with an "X" probe which is made visible, i.e., radioactive, fluorescent, etc. The mutant bacteriophages are traced on the plate and cloned on their new bacterial host. The ability of all clones to recognize "X" is determined on a solid phase through competitive assays with free "X" and for competition by "X" for the infection of bacteria by this mutant bacteriophage. Although the tail recognition of the receptor on bacteria may possess some similarity with antigen-antibody interactions, the bacteriophage recognition process possesses inherently different characteristics, thus rendering them surprising and unexpected replacements for antibodies. It is also unexpected that the bacteriophages are selected for the desired site recognition since host range mutations of the bacteriophage are known to be rather frequent The bacteriophages are made to recognize a particular antigen by other genetic manipulations. Bacteria are used that have some surface structures controlled by plasmids For example, the gene for "X" is incorporated in the plasmid. Bacteria which display "X" on their surface are then selected as described above. These surface proteins, or glycoproteins, are on structures used by the bacteriophage as receptors. By selecting bacteriophages that recognize these structures, as their infection receptors, bacteriophages are obtained that recognize "X". Accordingly, an external image of the antigen is obtained on bacteria.

Another approach is to make the bacteriophage tail have the same sequences as heavy and/or light chains of immunoglobulin, through recombination with immunoglobulin genes in plasmids. Parental bacteriophages with the normal tail sequences are removed by absorption with natural hosts. These are mutated and selected for recognition of "X" through the methods described above. A complete heavy and light chain arrangement is obtained by coinfecting bacteria having "X" on the surface with two bacteriophages, one expressing $V_H$ gene products and the other $V_L$ gene products.

In the practice of the method of this invention, one means involves assembling a kit, comprising an appropriate bacteriophage which is coupled with a visibility agent, for use in the identification of bacteria, eucaryotic cells, and other molecular materials. A number of portions of the phage can be afforded..,each in an amount selected to be effective in the contemplated assay.

The following examples are exemplary, without limitation, of the method of this invention.

EXAMPLE I-A

Bacteriophages are coupled to antibodies, monoclonal or polyclonal, after having been made fluorescent, radioactive, or coupled to peroxidase, and are used as a staining, or identification, agent. To detect mouse immunoglobulin G (MIG), the bacteriophage is coated with anti-MIG antibodies by using a coupling agent, e.g., glutaraldehyde or other bifunctional reagent. The phage is made fluorescent by coupling with fluorescein isothicyanate, rhodamine or other fluorescent dyes, by treatment with ethidium bromide, which binds to the phage DNA, or by other dyes that bind to nucleic acids. The phage is made radio-active either by incorporation of radioactive materials in its protein or nucleic acid or by conventional procedures of coupling radioactive materials to proteins. In the alternative, a metal such as silver is added to the phage by conventional procedures.

The bacteriophage suspension was preparted as follows: In a test example, bacteriophage $T_4$ was grown in YS57 strain of *Escherichia coli* (Trp, Pro, His). Bacteria were grown in tryptic soy broth (DIFCO) and mixed with phage for a multiplicity of infections of 0.5 to 1. The mixture of bacteria and bacteriophage was incubated in soft agar on a nutrient layer of hard agar. After overnight incubation, the bacteria were completely lysed by the phage, the top soft agar layer was collected and treated with chloroform and with 0.01M EDTA to precipitate the non-phage material. After 1 hour at 37° C., the mixture was centrifuged at 5000 G for 10 minutes and the supernatant was collected. To remove free nucleic acids, the supernatant was treated with 20 $\mu$g/ml. of DNAase and 20 $\mu$g/ml. of RNAase at 37° C. for 1 hour. To wash the phage, NaCl and polyethylene glycol (PEG) were added to final concentrations of 0.5M and 6%, respectively, and the mixture was incubated at 4° C. for 18 hours. After centrifugation at 8000 G for 30 minutes, and resuspension in 0.14M NaCl and 0.01M $MgCl_2$, there was obtained a final bacteriophage concentration of about $10^{13}$ infective units/ml The absorbance profile at different wave lengths was that of a pure phage population.

To coat antibodies, the following method was used. The phage, in suspension in 0.1M phosphate buffer at pH 8.5, was mixed with glutaraldehyde to a concentration of 1% and incubated at 25° C. for 1 hour. Excess glutaraldehyde was removed by precipitating the phage with 0.5M NaCl and 6% PEG and re-suspending in buffer at pH 8.5. Antibody, anti rabbit Ig was added to obtain 1 mg. antibody/1 mg. phage protein. After 2 hours incubation at 4° C. the phage was again washed by precipitation with PEG to remove unbound antibodies. The resulting phage was incubaged for 30 minutes at 4° C. with rabbit lymphocytes and the cells were washed three times by centrifugation at 900 G for 5 minutes.

The binding of the fluorescent phage was compared with that of fluorescent phage coated with either normal IgG instead of antibodies or with fluorescent anti Ig antibodies. The cells were examined under the fluorescence microscope. The cells with macrophage character (i.e., large) contained 2–5% phage particles in both normal Ig and anti Ig antibody preparations. However, the cell preparation treated with anti-Ig antibody-coated phage accounted for 47% of the cells with surface fluorescence while those treated with normal Ig-coated phage had only 1–2%.

The surface fluorescence was made more intense than that of the same cells treated with anti-Ig fluorescent antibodies. Thus, the anti-Ig antibody-coated phages showed specificity of binding and delivered intense fluorescence.

EXAMPLE I-B

Concentrated, purified bacteriophage is treated with a heterobifunctional reagent. Rabbit anti-allotype antibody (anti $b_4$) is thiolated and a bridge between the two is formed so that the rabbit antibody becomes coupled to the phage. As a control, the phage is then made fluorescent. The phage-antibody complex is then mixed with the cells, washed, and is examined, either with a microscope or other appropriate instrument. The degree of fluorescence is regulated through the degree of use of amino groups on phage proteins.

EXAMPLE I-C

The phage, coated with antibody, is employed to treat fixed tissue sections. A section of lymph node is treated with a fluorescent phage preparation, washed, and examined under UV light. In an alternate procedure, coated phage is revealed by final addition of the substrate according to standard methods. This method is also used for phages selected to bind spnntaneously.

EXAMPLE I-D

The phage, selected to recognize MIG either by the tail or by the head, is mixed with a solution containing MIG antibodies, e.g., monoclonal antibodies. This phage is either fluorescent or radioactive. After washing by precipitation with PEG, it is used to replace phages coupled chemically with antibody. The phages are made visible by an appropriate coupling procedure.

EXAMPLE II

Bacteriophages are designed to be used in rapid diagnosis of pathologic materials containing bacteria. Joint fluid or exudate is smeared, fixed, phages are added, and their presence visualized under proper instrumentation, such as UV light for fluorescence, bright field for enzymes, etc. By using automated computerized scanners the process is made very rapid. The binding of phages due to antiphage antibodies is avoided by competitive saturation with free phage protein or by treating the sample with formaldehyde. Very small numbers of bacteria, even if they are dead, are readily identified. Two-step addition of complex phage suspensions against a variety of possible pathogens, followed by individual suspensions in those products that appear positive, permits a rapid identification of rare micro- organisms.

To simulate the conditions of identification of bacteria in pathological samples the following experiment was performed.

$T_4$ bacteriophages were grown and purified as in Example I-A. Various amounts of fluorescein isothiocyanate (FITC), ranging from 0.5 mg. to 8 mg., were added per 1 mg. of phage protein. The phage suspension was adjusted to pH 9.3 with 0.1M $Na_2CO_3$. FITC was added with stirring at 4° C., stirring continued for 2 hours and then incubated at 4° C. for an additional 20 hours. Excess FITC was removed by dialyzing the suspension against 0.1M phosphate buffer (pH 8.5) at 4° C. for 3 days. The final molar ratios of FITC/protein in seven preparations were (1) 3.8, (2) 8.0, (3) 11.3, (4) 18.6, (5) 29.2, (6) 19.3, and (7) 16.4.

To determine the specificity of binding and ability to reveal the presence of one microorganism in a field, the $T_4$ phage which had been grown in *E. coli* strain YS57 was tested for binding to YS57. As controls, *E. coli* USC 106, which is a phage-resistant mutant of YS57, *Bacillus globigii* and *Salmonella schottmulleri* were used. To test for binding, phages were mixed with formaldehyde-fixed bacteria at 25° C. for 10 minutes and then washed 3 times to remove the unbound phage.

The phage sensitive *E. coli* YS57 became intensely fluorescent so that even one microorganism could be clearly seen under the fluorescence microscope. Phage preparations (1), (2) and (3), i.e., up to an FITC/protein molar ratio of 11.3, were made intensely florescent, while the mutant USC 106, *B. Globigii* and *S. schottmulleri* were not. However, phages labelled at molar ratios of 18.6 or more labelled all bacteria, including USC 106, *B. globigii* and *S. schottmulleri.* Thus, the phage specificity was maintained at a molar ratio of 11.3, which is similar to that routinely used for antibodies. However, since the phage particles have about 500 times more protein than do antibodies, the phage particles also provide that much more total fluorescence.

When fresh USC 106 and YS57 strains of *E. coli* were used (i.e., not fixed with formaldehyde) the phage bound equally to both bacteria. This was an unexpected finding, showing that the preparation should first be fixed with formaldehyde. This offers the advantage of destroying antibodies, particularly natural antibodies which may be present in pathologic preparations to be investigated and which may bind the phage.

EXAMPLE III-A

To obtain mutants of phages that recognize molecules and cells, the first condition is that the phage should not bind naturally to such cells or molecules. Thus, phages were prepared as in Example I-A and made fluorescent to a FITC/phage protein molar ratio of 11.3. These phages were tested for their ability to bind to complex cells, human lymphocytes treated with monoclonal mouse antibodies, and rabbit lymphocytes. Human mononuclear cells were purified from peripheral blood by the Ficoll-hypaque method, washed, and incubated at 4° C. for 1 hour with monoclonal mouse antihuman T cells, and washed again.

Rabbit lymphoid cells were obtained from spleen and lymph nodes by routine procedures, mixed and washed.

Suspensions containing $10^6$ cells/ml. (human or mouse) were treated with $10^{12}$ fluorescent phage particles, prepared as in Example I-A but not coated with any antibodies. After incubation at 4° C. for 1 hour, the cells were washed and examined under the microscope. No surface fluorescence was observed, indicating that $T_4$ bacteriophages, made fluorescent, do not stick non-specifically to either MIG, human lymphocytes, or rabbit lymphocytes. This surprising observation provided the basis for selecting for bacteriophages that bind.

The selection of bacteriophages that bind to structures other than those that they recognize naturally is done in two ways: by screening different existing bacteriophages from various collections and by snthetic manipulations. An example of screening is the following.

Bacteriophage $T_4$ does not bind to fresh suspensions of human or rabbit lymphocytes. To determine whether other structures of the blood elements can be identified, smears were prepared of rabbit and human blood cells and were treated with formaldehyde. The smears were then treated for 30 minutes with a suspension containing $10^{13}$ $T_4$ phage particles per ml. which were made fluorescent by treatment with FITC. The smears were washed, a cover slip placed on top, and examined under a fluorescent microscope. A very intense fluorescence was seen only in the cytoplasm of the leukocytes. The nucleus, the membrane, and the red blood cells were not fluorescent. This test shows that, somehow, through an unknown and unobvious mechanism, some structure in the cytoplasm of the white cells is recognized by the FITClabeled $T_4$ phage.

The selection of bacteriophages is also done through synthetic manipulations. In the preparation of bacteriophage mutants to recognize mouse immunoglobulin (IgG), *Escherichia coli,* strain YS57, are prepared in petri dishes, as in Example I-A, and are irradiated with UV light to obtain 50–90% killing of the bacteria; this step is done to trigger DNA repair mechanisms. A suspension of $T_4$ bacteriophage is also treated with UV light to kill about 80% of the bacteriophages and cause mutations. Bacteria are infected with the bacteriophage and the bacteriophage is grown, harvested and treated with chloroform. The phage suspension is then concentrated by precipitation with polyethylene glycol or by ultracentrifugation to obtain a suspension of over $10^{12}$ infective units/ml.

The bottom of a plastic petri dish is coated with mouse IgG (MIG) directly by incubation at 25° C. and pH 9.2 overnight, or by using poly-L-lysine as a coupling agent. This MIG does not have antiphage antibody activity, i.e., it is either monoclonal for another specificity or it is preabsorbed with phage or only the Fc portion is used. The phage is added to the dish and is incubated at 37° C. for 1 hour. The plate is carefully washed to remove any unbound phage. To improve the chance of obtaining the mutants, mouse IgG is attached to particles, erythrocytes, bacteria or beads, either chemically or through its antibody function.

The plate that is treated with phage and washed is used to grow the phage directly by adding bacteria in soft agar. The plate is first washed repeatedly to remove the phage that is not bound specifically. To improve the chance of obtaining head mutations that survive, the phage is also grown at higher temperatures, e.g., 42° C. The phage colonies are picked up and grown in susceptible bacteria and recloned 2–3 times.

As a prescreening for phage clones that recognize MIG the following method is used. Plates are coated with MIG as shown above, the parental strain of the phage is added in parallel with the mutants to different plates, incubated and washed, and finally bacteria are added. Although the parental strain gives only rare plaques, the mutants that bind to MIG give many plaques and even confluent lysis of bacteria.

EXAMPLE III-B

In a companion method to that of Example III-A, the phage colonies are picked up on an adsorbent paper. Either radioactive or fluorescent MIG is added, incubated to promote binding of MIG to the mutant, is washed and then examined, respectively, by a scanner for radioactivity or with UV light. The relevant mutants are retraced to the original gel and cloned. To obtain additional evidence all colonies formed are collected and grown in bacteria, each clone in two tubes, one containing aminoacids labelled with $14_C$. The phages are collected, treated with chloroform, collected by precipitation with polyethylene glycol or by ultracentrifugation, and are added to microwells coated with MIG. After incubation at 37° C. for one hour the wells are washed, sodium dodecylsulfate (SDS) solution is added to remove bound radioactive material and its c.p.m. determined. The phage clone that gives higher than background counts is then grown and retested for its ability to bind to MIG in the same system as above.

EXAMPLE III-C

The bacteriophage that demonstrates binding to MIG is made visible by any of the usual procedures. It is made fluorescent by coupling with fluorescein isothiocyanate, rhodamine or other fluorescent dyes, by treatment with ethidium bromide, which binds to the phage DNA, or by other dyes that bind to nucleic acids. The phage is made radioactive either by incorporation of radioactive materials in its protein or nucleic acid or by conventional procedures of coupling radioactive materials to proteins. In the alternative, a metal such as silver is added to the phage by conventional procedures.

To test the reagent value of this phage, human lymphocytes are treated with MIG anti-human T cell monoclonal antibodies. The cells are washed and, for example, the fluorescent phage is added. As a control the fluorescent phage is added to human lymphocytes not treated with the monoclonal antibody. After treating the lymphocytes for 30 minutes, they are washed and cells are examined under the microscope with UV light. The intense fluorescent staining of the 80–90% of the human peripheral blood lymphocytes demonstrates that the phage recognizes mouse IgG on the lymphocyte surface. The lack of fluorescence of cells treated with parental phage instead of the mutant, or pretreated with normal MIG instead of anti T cell antibody, offers a control. As another control, purified human B cells are shown not to become fluorescent when treated like the unseparated peripheral blood lymphocytes.

EXAMPLE IV

The selection of mutants by external imaging requires the preparation of bacteria that have phage receptors which mimic a certain macromolecule, e.g., mouse IgG (MIG), to be identified. In this case, MIG is injected into rabbits or rats to induce anti MIG antibodies. The following procedure is designed to make a bacteriophage work just like an antibody by using its tail as a combining site.

(1) The anti MIG antibody is purified by affinity chromatography and is coupled to a solid phase, such as the bottom of a petri dish, by using poly-L-lysine. *E. coli,* which is resistant to the phage, is grown, washed, suspended in physiologic buffered saline, added to the petri dish and is incubated at 4° C. for one hour. The petridish is carefully washed and culture medium is added. Bacteria that grow are exposed to the same binding cycle 4–5 times, each time in the presence of the phage to maintain the phage-resistant character of the bacteria. At each exposure bacteria are treated with mutagens to increase the number of mutants.

(2) Bacteria that are selected are cloned and each clone is tested for binding by the anti-MIG antibody by conventional methods. Bacterial mutants grow, when allowed to attach to the bottom of plates coated with the antibody against MIG, to a greater extent than the parental strain, thus providing a selective advantage to the mutant.

(3) The phage sensitive bacteria are UV irradiated, the phage is UV irradiated and is then mixed with phage-sensitive bacteria for infection and generation of mutants. However, the phages and bacteria can be first mixed and then UV irradiated. These bacteria are mixed in equal proportions with phage-resistant bacteria that are recognized by antiMIG antibodies. The phage lyses all phage-sensitive bacteria but does not affect the phage-esistant ones. When a mutant phage appears, which recognizes the MIG-like structure on the phage-resistant bacteria, a clear plaque is formed.

(4) The clear plaques are collected, grown in bacteria obtained in step 2 and each clone is tested for its interaction with MIG by routine competition or binding assays. The clones are tested for their ability to infect their host in the presence of MIG that has no antibody activity against the phage. When the phage recognizes MIG by its tail, it will bind to the MIG and will not be allowed to attach to its host. As a result no lysis occurs. By using fragments of MIG the precise site of recognition is determined.

The binding is tested on a solid phase coated with MIG, followed by peroxidase labelled anti-phage antibody and substrate. The characteristic change in color appears only where the phage is bound and shows its presence. The phage is visualized as in Example I.

EXAMPLE V

Some surface receptors, or antigens, on bacteria are controlled by plasmids. An example is the sex pilus on *E. coli.* This pilus is then recognized by sex-specific phages, such as OX174. The gene for the constant domain of either the heavy chain or the light chain of MIG is inserted into the plasmid that controls the sex pilus. Bacteria that express MIG in place of or together with pilus proteins are selected by using a solid phase with anti-MIG antibodies. Phages recognizing this pilus are then selected and shown to reocgnize MIG as before. In the first step the phage resistant bacteria are selected by the positive pressure of the anti MIG antibody. The phage is visualized as in Example I.

EXAMPLE VI-A

Bacteriophages are grown in bacteria that have variable genes of an antibody directed against MIG in plasmids. By recombination, phages are generated that express in the tail region of MIG heavy and/or light chains. By using the method of Example II, this phage grows preferentially in bacteria resistant to parental phage that have been selected to have on the surface the structure to be identified, e.g., MIG. This structure is expressed on the pilus as shown in Example III, or on other surface proteins that are used as receptors in infection.

EXAMPLE VI-B

*E. coli* containing L chain V genes of anti-MIG antibodies in plasmids are prepared according to standard procedures. Phages are grown in these bacteria to obtain recombinant DNA. Some phages have the $V_L$ or L genes expressed in the tail fiber but this event is incompatible with survival. The same procedure is applied for variable genes of heavy chains. To eliminate the parental phages, antibodies are made to be specific for tail fibers and all phages having expressed normal fibers are eliminated by absorption and precipitation with their host bacteria. Rare phages remain which are either defective or have H or L chains expressed. They are concentrated by ultracentrifugation and used to infect bacteria that express MIG, or MIG-like structures, on their surfaces as described above. By attraction through non-covalent forces, the phages expressing Ig genes infect their bacteria. The resulting progeny are "hybrid" phages, pairs of phages that will continue to cause coinfection. The specificity of this hybrid for MIG is determined as described above. The phage is visualized as in Example I.

EXAMPLE VII

Carbohydrates, either as mono, oligo, or polysaccharides, are coupled to bacteriophage which is then made fluorescent, radioactive or coupled to an enzyme. These probes are used to identify lectins in solution, with the aid of a fluorometer, on solid phase, or on cells. The phages are visualized as described in Example I.

EXAMPLE VIII

Lectins are coupled to bacteriophage which is made visible as in Example I. This conjugate phase is used to probe for carbohydrates for which the lectins are specific, either in solution, as in Example VII, on cells, or on solid phases.

We claim:

1. A method for preparing a bacteriophage binding through a head segment to molecular or cellular materials, comprising the steps of:

(a) mixing the bacteriophage, having both head and tail segments, with bacteria;
(b) irrading the mixture with ultraviolet light to effect mutation of the bacteriophage;
(c) nultiplying the mutant bacteriophage in the presence of bacteria binding through a tail segment to molecular of cellular material;
(d) purifying the population of nutant bacteriophage;
(e) binding the pruified mutant bacteriophage to the cellular material or to the molecular material; and
(f) multiplying the bound mutant bacteriophage in bacteria.

2. The method of claim 1 wherein the molecular material comprises immunoglobulins.

3. The method of claim 1 wherein the molecular material is coupled to a solid phase.

4. The method of claim 1 wherein the cellular material comprises surface glycoproteins of animal cells.

5. A method for preparing a selected bacteriophage binding through a tail segment to molecular or cellular materials, comprising the steps of:

(a) injecting molecular or cellular material into an animal host for the preparation of antibodies thereto;
(b) recovering and purifying said antibodies;
(c) coupling the purified antibodies to a solid phase;
(d) binding the coupled antibodies with bacteria characterized as being resistant to a selected bacteriophage;
(e) growing and harvesting the bacteria bound to said antibodies;
(f) irradiating selected bacteriophage binding through a tail sesgment to molecular of cellular material with ultraviolet light;
(g) separately irradiating a strain of bacteria, sensitive to the selected bacteriophage, with ultraviolet light;
(h) mixing the irradiated bacteriophage of step (f) with the irradiated bacteria of step (g);
(i) mixing approximately equal portions of the products of steps (e) and (h) under conditions for the development of plaques, whereby mutant bacteriophages are generated and yield clear plaques; and
(j) recovering the mutant bacteriophage from the clear plaques and multiplying it in the bacteria of step (e), whereby there is obtained a mutant bacteriophage capable of binding to said molecular or cellular materials.

6. The method of claim 5 wherein the molecular material comprises immunoglobulins.

* * * * *